United States Patent [19]

Lawes

[11] Patent Number: 5,047,057
[45] Date of Patent: Sep. 10, 1991

[54] TIBIAL COMPONENT FOR A REPLACEMENT KNEE PROSTHESIS

[76] Inventor: Peter Lawes, Pfizer Inc., 235 E. 42nd St., New York, N.Y. 10017-5755

[21] Appl. No.: 622,294

[22] Filed: Dec. 4, 1990

Related U.S. Application Data

[63] Continuation of Ser. No. 384,720, Jul. 25, 1989, abandoned.

[30] Foreign Application Priority Data

Jul. 27, 1988 [GB] United Kingdom ............... 8817908

[51] Int. Cl.$^5$ ............................................. A61F 2/38
[52] U.S. Cl. .................................................... 623/20
[58] Field of Search ...................... 623/20, 18, 16, 21

[56] References Cited

U.S. PATENT DOCUMENTS 4,714,474 12/1987 Brooks, Jr. et al. ................... 623/20
4,822,366 4/1989 Bolesky ............................... 623/20

FOREIGN PATENT DOCUMENTS 0021421 1/1981 European Pat. Off. .
0135319 3/1985 European Pat. Off. .
0288402 10/1988 European Pat. Off. .

OTHER PUBLICATIONS

"The Variable-Axis Knee Prosthesis" by David G. Murray, M.D. and Dwight A. Webster, M.D., in The Journal of Bone and Joint Surgery, vol. 63-A, No. 5, Jun. 1981, pp. 687-694.

Primary Examiner—Ronald Frinks
Attorney, Agent, or Firm—Peter C. Richardson; Lawrence C. Akers; Raymond W. Augustin

[57] ABSTRACT

A tibial component of a replacement knee prosthesis includes a tibial tray for connection to a suitably prepared tibia. The upper surface of the tray carries one or more bearing components provided with means for altering the position of the tibia relative to its co-operating femur by alternatively altering one or more of the following variables: medio-lateral offset, antero-posterior offset, antero-posterior tilt, tibial rotation and tibial condyle depression profile. The tray carries either one bearing component which cooperates with both femoral condyles, or two distinct bearing components, each of which cooperates with a single femoral condyle.

10 Claims, 2 Drawing Sheets

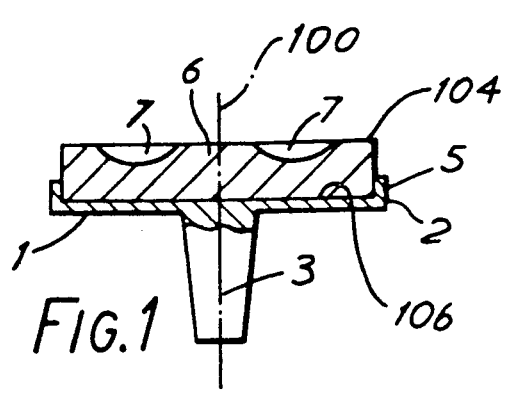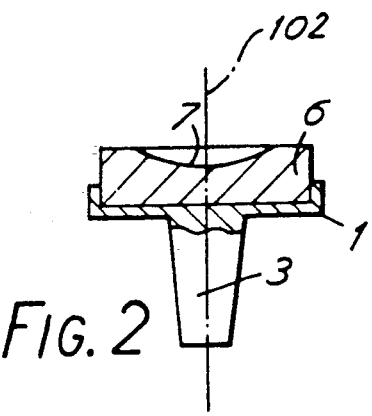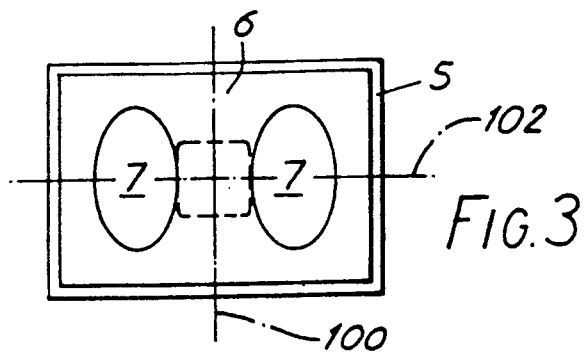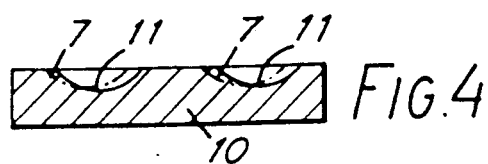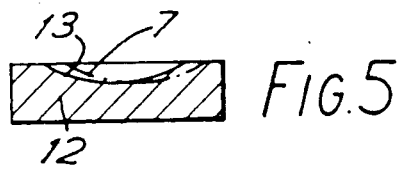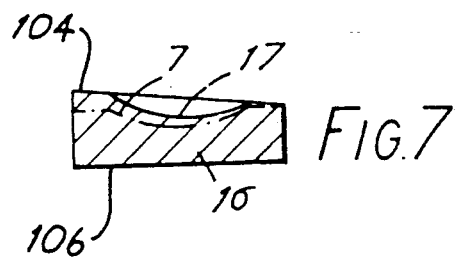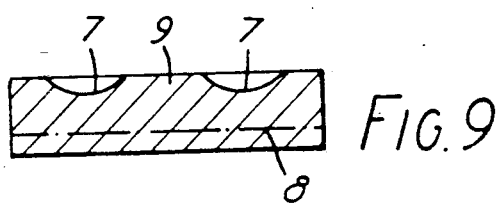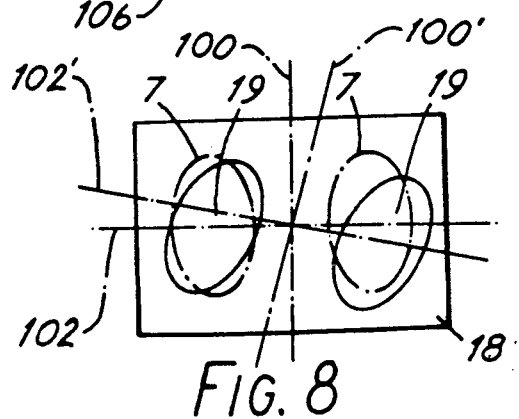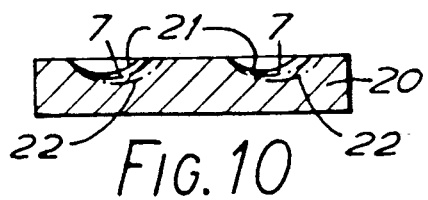

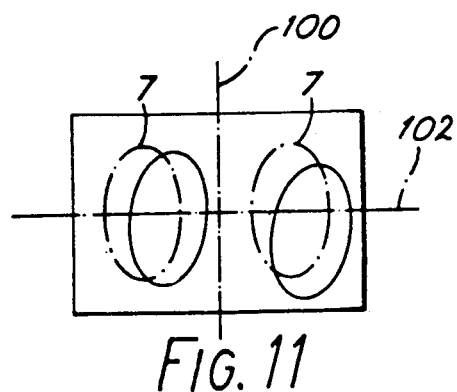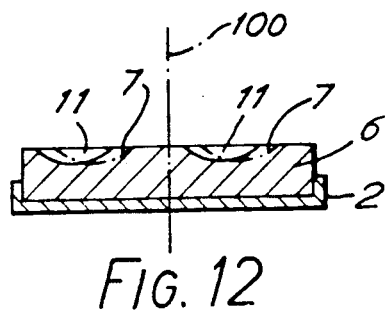
FIG. 11  FIG. 12
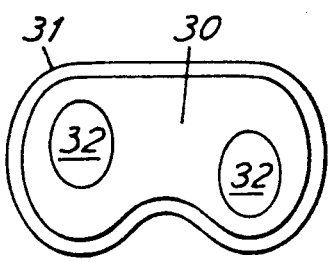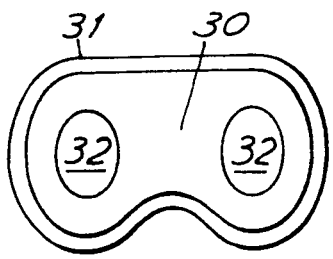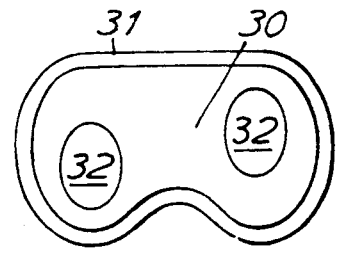
FIG. 14  FIG. 13  FIG. 15
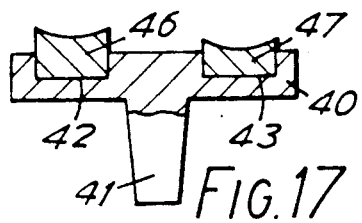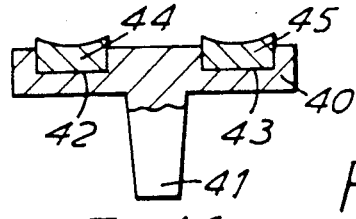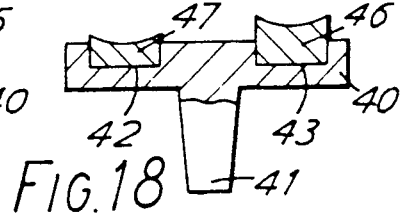
FIG. 17  FIG. 16  FIG. 18
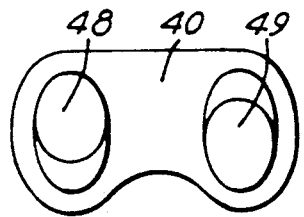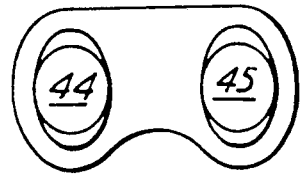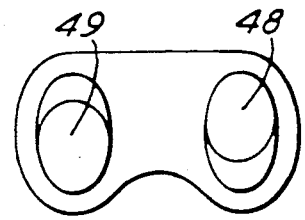
FIG. 21  FIG. 20  FIG. 22
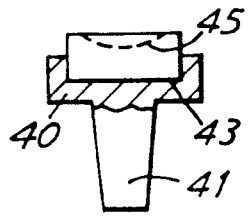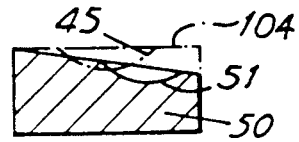
FIG. 19  FIG. 23

TIBIAL COMPONENT FOR A REPLACEMENT KNEE PROSTHESIS

This is a continuation of application Ser. No. 384,720, filed on July 25, 1989, now abandoned.

BACKGROUND OF THE INVENTION

This invention relates to a tibial component for a replacement knee prosthesis and can be used with the natural condyle bearing surfaces of a co-operating femur or with artificial condyles provided by a femoral prosthesis.

Tibial components comprising a metal tibial tray with removable and interchangeable synthetic plastics material bearing surface components of different thicknesses are available, the alternative bearing surfaces being provided so that the correct ligament tension can be achieved.

The femoral component of a surface replacement knee prosthesis is positioned and orientated mainly relative to the bone itself. There are three inner position variables: forward/backward, side to side, and vertically and there are three orientation variables: flexion/extension, varus/valgus, and rotation about the femoral shaft centerline. Additionally, the profile of the tibial condyle depressions affects the stability and locus of knee motions.

The tibial component is similarly positioned and orientated relative to the tibia.

When these components have been installed the only way a surgeon can at present adjust the knee is by choosing a bearing surface of different thickness to create the desired ligament tension or by removing the components and retrimming the bones.

If a surgeon therefore finds he has made a mistake, or changes his mind about the optimum knee alignment, there is no simple adjustment to be made. Furthermore, existing knee designs force a compromise in the horizontal positioning of both femoral and tibial components. The fixation must lie on or close to the outer cortical walls of the bone but this may not suit the ideal position for the bearing surface.

SUMMARY OF THE INVENTION

The present invention is intended to provide means for allowing a surgeon to alter the knee alignment during the operation.

According to the present invention a tibial component of a replacement knee prosthesis comprises a tibial tray for connection to a suitably prepared tibia, the upper surface of said tray carrying one or more bearing components, means for altering the position of the tibia relative to its cooperating femur by alternatively altering one or more of the following variables: medio-lateral offset, antero-posterior offset, antero-posterior tilt, tibial rotation or tibial condyle depression profile.

Means can also be included for altering a combination of any two of the offsets or tilts.

Preferably the means for altering the position of the tibia relative to its cooperating femur include two or more alternative bearing components one or more of which can be selected and located in the tray, said bearing components having alternative shaped and/or located bearing surfaces to receive the natural or artificial condyles of the cooperating femur.

A standard neutral bearing component is also preferably included in case no alteration is required.

Preferably the alternative bearing components provide alterations in at least medio-lateral tilt and antero-posterior tilt, these being the two most common variations required.

If desired the assembly may include bearing components for all alternative variables, or combinations thereof. For example, a component could be included which not only incorporated medio-lateral offset but also medio-lateral tilt and it will be appreciated that combinations of two or more of the variations can be incorporated.

In one preferred embodiment the tray carries a single bearing component having two shaped bearing surfaces, the variations being provided by alternative single components having bearing surfaces of different shapes and/or locations thereon.

In another embodiment according to the invention the tray carries two bearing components, each having a single shaped bearing surface to cooperate with a single condyle on the cooperating femur. Each component is selectable independently of the other from at least two alternative components having a bearing surface of different shape and/or location thereon.

Thus once the surgeon has implanted the bone fixation components on the femur and the tibia measurements or X-rays or computer assisted tomography scans can be produced and trial bearing components can be selected to check for correct joint movement and soft tissue tension. A definitive implantable bearing component can then be installed.

DETAILED DESCRIPTION OF THE INVENTION

The invention can be performed in various ways but one embodiment will now be described by way of example and with reference to the accompanying drawings in which:

FIG. 1 is a cross-sectional front elevation of a standard neutral tibial component for a replacement knee prosthesis;

FIG. 2 is a cross-sectional side elevation of the component shown in FIG. 1;

FIG. 3 is a top plan view of the component shown in FIG. 1;

FIG. 4 is a cross-sectional front elevation of an alternative bearing component shaped to provide medio-lateral offset;

FIG. 5 is a cross-sectional side view of a bearing component incorporating antero-posterior offset;

FIG. 6 is a cross-sectional front elevation of a bearing component incorporating medio-lateral tilt;

FIG. 7 is a cross-sectional side elevation of a bearing component incorporating antero-posterior tilt;

FIG. 8 is a top plan view of a bearing component incorporating tibial rotation;

FIG. 9 is a cross-sectional front elevation of a known kind of bearing component of variable thickness to adjust the height of the joint;

FIG. 10 is a cross-sectional front elevation of a bearing component incorporating tibial condyle depressions of different profile;

FIG. 11 is a top plan view of an alternative construction;

FIG. 12 is a cross-sectional front elevation of the bearing component shown in FIG. 4 but located in its tray in the opposite direction;

FIGS. 13, 14 and 15 are top plan views of an alternative tray shape;

FIG. 16 is a cross-sectional front view of an alternative construction;

FIGS. 17 and 18 are cross-sectional front views of the construction shown in FIG. 16 with alternative bearing inserts;

FIG. 19 is a cross-sectional side view of the construction shown in FIG. 16;

FIGS. 20, 21 and 22 are top plan views of the construction shown in FIGS. 16 and 19 with alternative bearing inserts; and FIG. 23 is a side elevation of an insert incorporating two variables.

FIGS. 1, 2 and 3 show a tibial component of a replacement knee prosthesis comprising a tibial tray 1 having an upper tray-like portion 2 and means for connecting the tray to a suitably prepared tibia provided by a spigot 3. Trays of this kind are well known in themselves and usually have raised tray walls 5. Mounted in the tray portion 2 is a bearing component 6 provided with two shaped bearing surfaces 7 which are in the form of depressions and which accommodate the condyles of the cooperating femur. Such condyles might be the natural condyles or artificial ones if provided on a cooperating femoral prosthesis component. The bearing component 6 may be a press fit in between the walls of the tray 5 or can be a snap fit or be held in place by any other arrangement, for example screws or pegs, or other means, and it may be desirable for it to be subsequently removable after fitting. The component is usually made from a synthetic plastics material.

In order to define reference points for the various offsets described below, various reference planes are shown on the figures. FIG. 1, a front view, is bisected by anterior-posterior plane (A-P) 100. FIG. 2, a side view, includes medial-lateral (M-L) plane 102 bisecting tibial tray 1. The A-P plane is a vertically extending plane which, for purpose of the description herein, runs through the center of the tibial tray 1 as measured along M-L plane 102 as shown in FIGS. 3, 8 and 11 (all plan views). Similarly, M-L plane 102 runs through the center of tibial tray 1 as measured along A-P plane 100. It should be noted that the M-L and A-P planes extending through tibial tray 1 coincide with or are parallel to the M-L and A-P planes bisecting the tibia depending on the size and shape of tibial tray 1. The reference system defined herein would apply to either the right or left knee prosthesis.

In the figures, surface 104 refers to the superior surface of bearing component 6 and surface 106 refers to the inferior surface of bearing component 6 which rests on tibial tray 1. As can be seen in FIG. 8, the depressions 7 can be rotated such that perpendicular planes 100' and 102' are angularly offset with respect to planes 100, 102.

Configuration and location of the bearing surfaces dictate the optimum knee alignment.

It is known to provide a bearing component as shown in FIG. 9 in which the same reference numerals are used to indicate similar parts. In FIG. 9 the depth of the standard component is indicated by broken line 8 and it will be seen that the thickness of the component as shown in FIG. 9 is somewhat greater.

After a tibial component of the kind shown in FIG. 1 had been installed the one way a surgeon could adjust the knee prior to the present invention was by replacing the bearing component 6 as shown in FIG. 1 by a bearing component 9 as shown in FIG. 9 to create the desired ligament tension. The only other alternative is by removing the components and retrimming the bones. If therefore a surgeon finds he has made a mistake or changes his mind about the optimum knee alignment there is no simple adjustment to be made. It has also been proposed to provide a bearing component as shown in FIG. 6 to provide alternative variations in medio-lateral tilt, the bearing surfaces being indicated by reference numeral 15 and the original standard bearing surfaces being again indicated by reference numeral 7.

The present invention however provides a number of alternative bearing components which can be inserted into the tray 2 to replace the standard component 6 thus permitting a relative adjustment of the tibia relative to the femur. FIG. 4 shows a bearing component 10 of similar overall shape to the component 6 in which the bearing surfaces indicated by reference numeral 11 are provided with medio-lateral offset. The position of the standard bearing surfaces are indicated in broken lines by reference numeral 7. This medio-lateral offset is very important for establishing knee alignment.

FIG. 5 shows a bearing component 12 in which the bearing surfaces 13 have antero-posterior offset which again is an important variation in providing optimum knee alignment. Once again the position of the standard bearing surfaces is indicated in broken lines by reference numeral 7.

FIG. 7 shows a bearing component 16 in which the bearing surfaces 17 incorporate antero-posterior tilt. Once again the standard bearing surfaces 7 are indicated by a broken line.

The bearing component 18 shown in FIG. 8 is provided with bearing surfaces 19 to provide for tibial rotation to accommodate for foot pointing, pigeon toes or wide spread toes and again is an important aspect of optimum knee alignment.

FIG. 10 shows a bearing component in which the bearing surfaces 21 are of a different profile to the standard bearing surfaces, again indicated by reference numeral 7. The bearing surfaces 21, which provide the tibial condyle depression, affect the stability of the knee and the locus of knee motion. Thus they may have different shapes affecting for example the height of the outer rim at different locations and the profile slope to provide the desired effect. As shown in FIG. 10 another alternative profile is shown by broken lines 22 which provide a deeper depression with higher rims.

A kit for setting up a tibial component according to the invention can incorporate any of the alternative bearing components shown in the drawings and preferably includes at least two of them. A standard component 6 may of course also be incorporated.

Perhaps the most important alternative bearing components are those shown in FIGS. 6 and 7 to accommodate medio-lateral tilt and anterio-posterior tilt as these two variations tend to be the most common.

Further or alternative bearing components can be provided which incorporate simultaneously two of the alternative bearing surface configurations. Thus components can be provided which incorporate not only medio-lateral offset as shown in FIG. 4 but also tibial rotation as shown in FIG. 8. The same component can even be provided in different thicknesses as shown in FIG. 9. It will be appreciated that there are many combinations which can be provided and which can be used for special requirements. FIG. 11 is a plan view showing the combination of medio-lateral offset and tibial rotation.

The dimensions have been exaggerated to make them more clear.

As will be seen from the drawings the tray is substantially rectangular in plan view and in certain circumstances it is possible to provide variations by reversing the bearing component 6. Thus FIG. 12 shows the same component as FIG. 4 but inserted in the opposite way so that the medio-lateral offset, which is shown to the right in FIG. 4, now appears to the left. This reversal is possible due to the symmetrical shape of the tray and can be employed with the other inserts as well.

In FIGS. 13, 14 and 15 three plan views are shown of an alternative tray shape. In each case there is an insert 30 carried in a flanged tray 31. The bearing surfaces 32 are shown in FIG. 13 in a neutral position, in FIG. 14 in a toe in position, and in FIG. 15 in a toe out position. Once again any of these constructions could also incorporate one or more of the other configurations, for example, antero-posterior offset and alternative depths.

It will be appreciated that with the constructions referred to above a considerable number of variations and different sizes and configurations can be produced and FIGS. 16 to 23 show an alternative construction which provides easy variations but at reduced cost in as much that the range of inserts can be reduced.

In this type of construction the tibial tray 1 is replaced by a component having an upper tray-like head 40 connected to a spigot 41. The upper surface of the tray is provided with two spaced apart depressions 42, 43 which are generally of oval shape in plan view and into which a pair of bearing components 44, 45 can be snapped into place. Other arrangements could be employed, for example screws or pegs, or other means, to hold the bearing components 44, 45 in place. Once again the components will usually be made of a synthetic plastics material.

FIGS. 16, 19 and 20 show standard inserts in which the bearing surfaces are in neutral or standard positions. FIG. 17 shows inserts which are shaped to provide medio-lateral tilt to one direction and FIG. 18 shows the tilt in the other direction. The tilt may be provided by either a taller insert 46 in place of the standard insert 44 or by a shorter insert 47 in place of the standard insert 45. It is possible to thus employ a standard insert 44, 45 on one side and a modified insert on the other and thus various combinations can be produced as required.

In FIGS. 21 and 22 the bearing surfaces are shaped and located to provide for tibial rotation. Thus FIG. 21 shows toe in with appropriate inserts 48 and 49. The amount of toe in could be reduced by using a standard insert 45 in place of insert 49. Similarly, in FIG. 22 the insert 49 can be placed in the position of insert 48 with the insert 48 replacing the insert 49 to provide a construction for toe out. FIG. 20 shows inserts 44 and 45 providing the neutral position.

A range of inserts can be provided for medio and lateral offset and the other variations referred to with regard to the first type of construction but with this arrangement it will be appreciated that the number of inserts required can be reduced as they can usually be rotated to the opposite position due to the oval shape of the depressions 43 to enable them to be placed not only on opposite sides of the tray 40 but in reversed positions fore and aft.

Once again each insert 44 and 45 can incorporate two or more of the variations and FIG. 23 shows an insert 50 which shows in broken lines the position of the bearing surface as, for example, in the neutral insert 45. In this insert however the bearing surface 51 is not only provided with antero-posterior offset but also with antero-posterior tilt.

I claim:

1. A surgically implantable knee joint prosthesis for the replacement of the articulation surfaces of a proximal tibia comprising:
   a base plate having an upper surface and a lower surface adapted to be permanently fixed to a surgically prepared superior surface of the proximal tibia, said base plate bisected by a medial-lateral plane (M-L) and an anterior-posterior (A-P) plane;
   an articulation insert fixedly attached to said upper surface of said base plate, said insert having a superior surface having at least one depression having a central axis therethrough and configured to receive a corresponding condyle present on a distal femur, a vertical plane containing said axis of said depression extending along said insert being non-coplanar with respect to said anterior-posterior (A-P) plane and a medial-lateral (M-L) plane extending through the base plate.

2. The prosthesis set forth in claim 1 wherein a plane containing said superior surface is perpendicular to both the M-L and A-P planes.

3. The prosthesis as set forth in claim 1 wherein said superior surface is sloped in the superior-inferior direction with respect to at least one of the M-L and A-P planes.

4. The prosthesis as set forth in claim 2 wherein said vertical plane is angularly offset with respect to said M-L and A-P planes.

5. The prosthesis as set forth in claim 1 wherein said articulation insert has two depressions on said superior surface, each having spaced apart centers, a line connecting said centers and a vertical plane containing said line being angularly offset with respect to at least one of said M-L and A-P planes.

6. A surgically implantable knee joint prosthesis for the replacement of the articulation surfaces of a proximal tibia comprising:
   a base plate having an upper surface and a lower surface adapted to be permanently fixed to a surgically prepared superior surface of the proximal tibia, said tibial tray bisected by a medial-lateral plane (M-L) and an anterior-posterior (A-P) plane;
   an articulation insert fixedly attached to said upper surface of said base plate, said insert having a superior surface having two depressions therein to receive corresponding condyles present on a distal femur, said depressions having spaced apart centers and a line connecting said centers and a vertical plane containing said line being non-coplanar with said medial-lateral (M-L) plane bisecting the tibial tray.

7. The prosthesis set forth in claim 6 wherein a plane containing said superior surface is perpendicular to both the M-L and A-P planes bisecting the tibial tray.

8. The prosthesis as set forth in claim 6 wherein said superior surface is sloped in the superior-inferior direction with respect to at least one of the M-L and A-P planes.

9. The prosthesis as set forth in claim 6 wherein said vertical plane containing said line is parallel to said M-L plane.

10. The prosthesis as set forth in claim 6 wherein said vertical plane containing said line intersects said M-L plane.

* * * * *